(12) United States Patent
Shi et al.

(10) Patent No.: US 11,180,795 B1
(45) Date of Patent: Nov. 23, 2021

(54) NEMATODE RESISTANCE ALLELES IN SOYBEAN

(71) Applicant: Syngenta Participations AG, Basel (CH)

(72) Inventors: Ainong Shi, Fayetteville, AR (US); Becky Welsh Breitinger, Research Triangle Park, NC (US); Ju-Kyung Yu, Research Triangle Park, NC (US); Azhaguvel Perumal, Slater, IA (US)

(73) Assignee: Syngenta Participations AG, Basel (CH)

( * ) Notice: Subject to any disclaimer, the term of this patent is extended or adjusted under 35 U.S.C. 154(b) by 575 days.

(21) Appl. No.: 15/171,078

(22) Filed: Jun. 2, 2016

Related U.S. Application Data

(60) Provisional application No. 62/169,739, filed on Jun. 2, 2015.

(51) Int. Cl.
*C12Q 1/6827* (2018.01)
*C12N 15/82* (2006.01)
*A01H 1/02* (2006.01)
*C12Q 1/6895* (2018.01)

(52) U.S. Cl.
CPC .......... *C12Q 1/6827* (2013.01); *A01H 1/02* (2013.01); *C12N 15/8285* (2013.01); *C12Q 1/6895* (2013.01); *C12Q 2600/13* (2013.01); *C12Q 2600/156* (2013.01)

(58) Field of Classification Search
CPC .................................................. C12Q 1/6827
See application file for complete search history.

(56) References Cited

U.S. PATENT DOCUMENTS

| | | | |
|---|---|---|---|
| 5,491,081 A | 2/1996 | Webb | |
| 6,300,541 B1 | 10/2001 | Lightfoot et al. | |
| 7,154,021 B2 | 12/2006 | Hauge et al. | |
| 7,485,770 B2 | 2/2009 | Hauge et al. | |
| 7,872,171 B2 | 1/2011 | Webb | |
| 2006/0225150 A1 | 10/2006 | Hauge et al. | |
| 2006/0253919 A1 | 11/2006 | Hauge et al. | |
| 2008/0072352 A1 | 3/2008 | Lightfoot et al. | |
| 2009/0100537 A1 | 4/2009 | Concibido et al. | |
| 2010/0275320 A1 | 10/2010 | Lightfoot et al. | |
| 2012/0278953 A1 | 11/2012 | Webb | |
| 2013/0340115 A1* | 12/2013 | Daines ................. | C12Q 1/6895 800/279 |
| 2014/0182009 A1 | 6/2014 | Allen et al. | |
| 2014/0215657 A1 | 7/2014 | Nguyen et al. | |
| 2016/0130671 A1 | 5/2016 | Shendelman et al. | |

* cited by examiner

*Primary Examiner* — David H Kruse
(74) *Attorney, Agent, or Firm* — Suparna Kanjilal

(57) ABSTRACT

Methods for conveying soy cyst nematode (SCN) resistance into non-resistant soybean germplasm are provided. In some embodiments, the methods include introgression SCN resistance into a non-resistant soybean using one or more nucleic acid markers for marker-assisted breeding among soybean lines to be used in a soybean breeding program, wherein the markers are linked to and/or associated with SCN resistance. Also provided are single nucleotide polymorphisms (SNPs) associated with resistance to SCN. Soybean plants and seeds produced by any of the disclosed methods are provided.

5 Claims, No Drawings

Specification includes a Sequence Listing.

NEMATODE RESISTANCE ALLELES IN SOYBEAN

RELATED APPLICATION INFORMATION

This application claims the benefit of U.S. Provisional Application No. 62/169,739, filed 2 Jun. 2015, the contents of which are incorporated herein by reference herein.

FIELD OF THE INVENTION

The present invention relates to compositions and methods for identifying, selecting and/or producing soybean plants having tolerance to soy cyst nematode.

STATEMENT REGARDING ELECTRONIC SUBMISSION OF A SEQUENCE LISTING

A Sequence Listing in ASCII text format, submitted under 37 C.F.R. § 1.821, entitled "80814_ST25" generated on Jan. 21, 2021; ~24 kb in size, and filed via EFS-Web is provided in lieu of a paper copy. This Sequence Listing is hereby incorporated by reference into the specification for its disclosures.

BACKGROUND

Soybean (*Glycine max* L. Merr) is a major cash crop and investment commodity in North America and elsewhere. Soybean oil is one of the most widely used edible oils, and soybeans are used worldwide both in animal feed and in human food production. The soybean cyst nematode (herein "SCN") is a small, plant-parasitic roundworm that attacks the roots of soybean plants. Responsible for causing annual losses of approximately $1.5 billion for U.S. growers, SCN has become a widespread problem across all major production areas. Nematodes not only directly rob soybeans of yield, but by feeding on the roots, they allow entry points of access for other plant pathogens. SCN damage is often misdiagnosed or confused with other crop production problems and can increase incidence of other soybean disease pests.

Historically, soybean growers used various nematicides to fight SCN. About 30 years ago, the industry began using native trait (NT) SCN resistance derived from Plant Introductions (PI) from Asia. Most of the soybean varieties feature soybean cyst nematode protection derived from PI 88788. The resistance loci from PI 88788 are found in about 95% of soybean varieties with SCN resistance. PI 88788 has no other known redeeming agronomic value to offer except for the few traits that confer SCN resistance. However, in recent years, this leading source of NT resistance against soybean cyst nematode has been weakening due to increased resistance of the pathogen. As varieties with PI88788 resistance get used continuously across soybean acres, farmers are seeing an increase in other SCN races that are immune to the PI88788 source of resistance. Different varieties of soybean vary in their sensitivity or tolerance to soy cyst nematode. Therefore a key importance in the control of SCN is to discover new sources and alleles that may be bred into commercial soy lines.

SUMMARY OF THE INVENTION

Definitions

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker (e.g., SNP, QTL, haplotype) can mean one marker or a plurality of markers (e.g., 2, 3, 4, 5, 6, and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with tolerance to SCN in a soybean plant relative to a control soybean plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with an SCN tolerance allele" refers to a marker whose presence or absence can be used to predict whether a plant will display tolerance to SCN.

As used herein, the term "SCN plant" or "SCN tolerance" refers to a plant's ability to endure and/or thrive despite being exposed to growth conditions in which SCN are low as compared to one or more control plants (e.g., a plant lacking a marker associated with SCN).

Thus, "tolerance" in a soybean plant to SCN conditions is an indication that the soybean plant is less affected by the SCN conditions with respect to yield, survivability and/or other relevant agronomic measures, compared to a less tolerant, more "susceptible" plant. Tolerance is a relative term, indicating that a "tolerant" soybean plant survives and/or produces a better yield in SCN growth conditions when compared to a different (less tolerant) soybean plant (e.g., a different soybean strain or variety) grown in similar conditions. A tolerant plant can have a greater survival rate and/or yield, as compared to a soybean plant that is susceptible or intolerant to these SCN growth conditions. SCN "tolerance" sometimes can be used interchangeably with SCN "resistance." SCN intolerant soybean varieties and cultivars are well known in the art.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example, in* TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding, in* PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with SCN tolerance may be introgressed from a donor into a recurrent parent that is SCN intolerant. The resulting offspring could then be backcrossed one or more times and selected until the progeny possess the genetic marker(s) associated with SCN tolerance in the recurrent parent background.

As used herein, the term "linkage" refers to the degree with which one marker locus is associated with another marker locus or some other. The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., SCN. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234: 177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase internet resource (www.soybase.org). In some embodiments, a genetic marker of this invention is an SNP allele, a SNP allele located in a chromosome interval and/or a haplotype (combination of SNP alleles) each of which is associated with SCN tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Table 1).

Accordingly, in some embodiments of this invention, a marker is detected by amplifying a Glycine sp. nucleic acid with two oligonucleotide primers by, for example, the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules.

Some of the markers described herein can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual*, Third Edition, Cold Spring Harbor Laboratory Press, Cold Spring Harbor, N.Y., United States of America. Generally, lower salt concentration and higher temperature hybridization and/or washes increase the stringency of hybridization conditions.

As used herein, the term "probe" refers to a single-stranded oligonucleotide sequence that will form a hydrogen-bonded duplex with a complementary sequence in a target nucleic acid sequence analyte or its cDNA derivative.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and for polynucleotide sequence BLASTN can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "soybean" refers to a plant, and any part thereof, of the genus *Glycine* including, but not limited to *Glycine max*.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny", "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

As used herein, the term "reference sequence" refers to a defined nucleotide sequence used as a basis for nucleotide sequence comparison. The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

Genetic Mapping

Genetic loci correlating with particular phenotypes, such as SCN tolerance can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with SCN tolerance in soybean. Detection of these markers and/or other linked markers can be used to identify, select and/or produce soybean plants having SCN tolerance and/or to eliminate soybean plants from breeding programs or from planting that do not have SCN tolerance.

Markers Associated with SCN Tolerance

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) Methods in Plant Molecular Biology and Biotechnology, CRC Press, Boca Raton, Fla., United States of America; Zietkiewicz et al. (1994) Genomics 20:176-183.

In one embodiment of the invention involves a method of identifying or selecting soybean lines having increased resistance to SCN wherein a molecular marker as indicated in Table 1 is detected in a soybean genomic DNA sample and used to identify and/or select a SCN line having resistance to SCN.

In another embodiment, the invention provides methods of producing soybean lines having increased resistance to SCN wherein a soybean plant comprising any marker listed in Table 1 is crossed with a soybean plant not comprising said respective marker thus creating a progeny plant comprising said respective marker. In a preferred embodiment the marker is derived from any one of soybean lines PI494182, PI507354, PI467312, PI548317, PI89772, PI5675160, PI507422, CE1210290 or a progeny thereof.

In addition to the markers detailed in Table 1, it is contemplated that the following SNP markers would be useful in selecting, identifying or producing soybean lines resistant to SCN (positions correspond to 8× public build of the Williams82 soybean genome at the SoyBase internet resource (soybase.org/SequenceIntro.php) or USDA at (bfgl.anri.barc.usda.gov/cgi-bin/soybean/Linkage.pl): Chromosome 11 at position 37073829 having a A; Chromosome 11 at position 37112108 having a G; Chromosome 11 at position 37335482 having a A; Chromosome 11 at position 37496850 having a G; Chromosome 11 at position 37863691 having a G; Chromosome 11 at position 38221754 having a G; Chromosome 8 at position 8219013 having a C; Chromosome 8 at position 8251158 having a C; or Chromosome 8 at position 8281297 having a T. It is contemplated that any one of these markers & loci associated with these markers may be derived from any one of soybean lines PI494182, PI507354, PI467312, PI548317, PI89772, PI567516C, PI507422, CE1210290 or a progeny thereof.

In another embodiment of the invention is provided an elite soybean plant produced by crossing soybean line CE121029 with a second soybean plant wherein said cross results in a SCN resistant plant. In a preferred embodiment the second soybean plant has introgressed into its genome a SCN resistant loci that associates with any one of the molecular markers as demonstrated in Table 1 or any one SNP marker corresponding with Chromosome 11 at position 37073829 having a A; Chromosome 11 at position 37112108 having a G; Chromosome 11 at position 37335482 having a A; Chromosome 11 at position 37496850 having a G; Chromosome 11 at position 37863691 having a G; Chromosome 11 at position 38221754 having a G; Chromosome 8 at position 8219013 having a C; Chromosome 8 at position 8251158 having a C; or Chromosome 8 at position 8281297 having a T.

Table 1 provides information about the SCN tolerance/resistant associated markers presented including the physical location of the marker on the respective CE1210290 soybean chromosome, and the target allele that is associated with soy cyst nematode tolerance/resistance. Markers of the present invention are described herein with respect to the positions of marker loci in the 8× public build of the Williams82 soybean genome at the SoyBase internet resource (soybase.org/SequenceIntro.php) or USDA at (bfgl.anri.barc.usda.gov/cgi-bin/soybean/Linkage.pl)

TABLE 1

The respective soybean chromosome AND physical positions comprising the favorable allele associated with increased resistance to each respective SCN race.

| Marker I.D. (SEQ ID NO:) | Soy Chromosome | Physical Position of Marker | Favorable Allele | Unfavorable Allele | SCN Race Resistance |
|---|---|---|---|---|---|
| 1 (12) | 18 | 1638718 | G | A | 1, 3 & 5 |
| 2 | 18 | 1690438 | G | A | 1, 3 & 5 |
| 3 (7) | 18 | 1712035 | C | A | 1, 3 & 5 |
| 4 (8) | 18 | 1712922 | G | A | 1, 3 & 5 |
| 5 | 18 | 1735950 | C | G | 1, 3 & 5 |
| 6 | 18 | 1736100 | A | C | 1, 3 & 5 |
| 7 (2) | 18 | 1736136 | G | A | 1, 3 & 5 |

TABLE 1-continued

The respective soybean chromosome AND physical positions comprising the favorable allele associated with increased resistance to each respective SCN race.

| Marker I.D. (SEQ ID NO:) | Soy Chromosome | Physical Position of Marker | Favorable Allele | Unfavorable Allele | SCN Race Resistance |
|---|---|---|---|---|---|
| 8 | 19 | 37734309 | A | G | 2 |
| 9 | 19 | 37877119 | G | A | 2 |

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A method of identifying or selecting an SCN tolerant soybean plant or part thereof, comprising the steps of
   a) isolating a nucleic acid from a first soybean plant;
   b) detecting in the nucleic acid of a) a molecular marker associated with increased SCN resistance using primers capable of amplifying the molecular marker by polymerase chain reaction, wherein said molecular marker is at least one of: on Chromosome 18, a G at position 1638718 corresponding to position 251 in SEQ ID NO: 12; on Chromosome 18, a G at position 1712922 corresponding to position 301 in SEQ ID NO: 8; on Chromosome 18, a G at position 1736136 corresponding to position 274 in SEQ ID NO: 2; and
   c) thereby identifying or selecting a SCN tolerant soybean plant or part thereof.

2. A method of identifying or selecting an SCN tolerant soybean plant or part thereof, comprising the steps of
   a) isolating a nucleic acid from a first soybean plant;
   b) detecting in the nucleic acid of a) a molecular marker within a chromosomal interval associated with increased SCN resistance using primers capable of amplifying the molecular marker by polymerase chain reaction, wherein said chromosomal interval is from position 37734309 to position 37877119 on Chromosome 19 with reference to the 8× public build of Williams82 soybean genome, and includes a G at position 37877119 and a A at position 37734309; and
   c) thereby identifying or selecting a SCN tolerant soybean plant or part thereof.

3. A method of identifying or selecting an SCN tolerant soybean plant or part thereof, comprising the steps of
   a) isolating a nucleic acid from a first soybean plant;
   b) detecting in the nucleic acid of a) a molecular marker associated with increased SCN resistance using primers capable of amplifying the molecular marker by polymerase chain reaction, wherein said molecular marker is located within an interval on Chromosome 18 defined by a G at position 1638718 corresponding to position 251 in SEQ ID NO: 12 and a G at position 1736136 corresponding to position 274 in SEQ ID NO: 2;
   c) thereby identifying or selecting a SCN tolerant soybean plant or part thereof.

4. The method of claim 3, further comprising crossing the identified or selected plant having increased SCN resistance with a plant not containing the marker, thereby producing a new plant having increased SCN resistance.

5. A method of identifying or selecting an SCN tolerant soybean plant or part thereof, comprising the steps of
   a) isolating a nucleic acid from a first soybean plant;
   b) detecting in the nucleic acid of a) a molecular marker associated with increased SCN resistance using primers capable of amplifying the molecular marker by polymerase chain reaction, wherein said molecular marker is at least one of, with reference to the 8× public build of Williams82 soybean genome: on Chromosome 18, a G at position 1690438; on Chromosome 18, a C at position 1735950; and on Chromosome 18, an A at position 1736100; and
   c) thereby identifying or selecting a SCN tolerant soybean plant or part thereof.

* * * * *

SEQUENCE LISTING

```
<160> NUMBER OF SEQ ID NOS: 60

<210> SEQ ID NO 1
<211> LENGTH: 1353
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (292)..(292)
<223> OTHER INFORMATION: n = a or c
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t

<400> SEQUENCE: 1
agagatataa agctccaaat ctcagaccct cgaatgcaca tgctaaacgc aaaaacaaca      60
gtgatggcca caagcccaca acaactagta gaaaattttc ttaatctcaa cacccaagca     120
cttggttttt atggtattaa tattagtaat acacacaaaa ccacgaacac aatgagggac     180
caaattaggt caccgaagca tatagtccac aacacagcga aagccacttc atcaatttct     240
acgaatttcc ttaaaaaaat tcaaaactac attatcaggg gtttgactcg tnacactttg     300
tgactataaa tggcatctac aataacgata aatgaatagt tacagtgtat agagcatatc     360
gcagatcacg aaatagaaga aatcgaaaga ataaggacct gatcagaaaa tggagaactg     420
gcaatgtgcg gttgccggcg ggaagaacca acggcgttta gggtttgggc tatgaaggga     480
atggaaagga aaggcagagt gaagcaaact gntgaatcga acgcaagctt cactcatcat     540
tctgctacca gaatttagtt taaacaaatt aagataaaca ataataataa taataataat     600
aataataata ataataataa taataataat ttatatatta aattaaagaa aaaaatanct     660
gatgtgttaa aattgagagg aaaaaaagaa tctaaactat gatccattac ttcaaatctt     720
```

-continued

| | |
|---|---|
| caatatgggt tttaaacaaa aatattttta tttattaaaa tagtttagta tatatttatg | 780 |
| ataaaaatat taagtttaat tgtcatgtat ttatcaatgt aaactttcag ttctgttaga | 840 |
| aattgttccc agtatgacta caagatggtt acttatgaaa ataaaaaaa atattatata | 900 |
| tgaaaattta aaatccatag taagaaatg tttttaaact ataagttata ttttttaatt | 960 |
| tataataaat aattcacatt gtgaaccttta tttttctaa tatcaataat tgttttaaaa | 1020 |
| aaatgttgaa attcaattta aaattaaga tgaaaaatat aagaaattaa gaaaaccaag | 1080 |
| tgaacaatta caaataaaga taaatcataa taatttgaga tgatggaaaa ataaattttt | 1140 |
| ggggataata gttaaatcaa attaaaaaat atatatttaa aagtaataaa aaataaaatg | 1200 |
| taaactaaaa gcttaatata acaaattagg acaaggcatg taactcaatg tgaatgataa | 1260 |
| taattcttaa aattgcttcc atgtaagaaa aactactaaa aacattataa ttgctagtga | 1320 |
| aaatattcgt ctaaattata catgggtggg ctg | 1353 |

```
<210> SEQ ID NO 2
<211> LENGTH: 716
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (274)..(274)
<223> OTHER INFORMATION: n = a or g
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t

<400> SEQUENCE: 2
```

| | |
|---|---|
| gaaactaaaa aaaccttaaa taaaacccga aactaattag ttttctcatt tttcttccta | 60 |
| aacttttatt attattatta ttattattat tattattatt attntgactt aantactggg | 120 |
| aaccaaaacg agaaaaaaga cgccaatttg aaggactcga attaaatcat aaaaaaatca | 180 |
| aaatttattt gactcttcca taactttggg gattaaaata acactgaaat ataaactcaa | 240 |
| gcactaattc atttaaaaaa acattgaaaa tgcnttgtat gtacaataca tcaaatcaaa | 300 |
| tctaattan gttattatta cgttttgtag atgttggatg aggatacatt cagtcaattg | 360 |
| gtgttctgtg tggtacttat aaccgcgatt gtaacaccct tggttaacat attgtacaag | 420 |
| catcgccctc gagtacacgc agaaagctta ttcgaagggn aactgagaac gatccaaagc | 480 |
| actccaagaa acagagagtt tcacattgtt tgttgtgtac ataatgaagc aaacgtgcgt | 540 |
| ggcatcactg ccttattaga agagtgcaac ccagtgcaag agagccccat atgcgtctac | 600 |

```
gcagtccacc ttatcgagct cgtggggaaa agtgcaccca ttctccttcc cataaaacat    660
agacacggtn gcagaaaatt cttgtctgtg aattacccca ncccaaaaac tcgaaa        716
```

<210> SEQ ID NO 3
<211> LENGTH: 337
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (206)..(206)
<223> OTHER INFORMATION: n = c or g

<400> SEQUENCE: 3

```
ctgatattca gttttccagg ctaagctgag atatatttta tatccctctt aaaaacaatt     60
ccaagatgag aggatatctg ctttgaccct tcaattgcag gattatccgc caggttgaat    120
gacttctttt tcaacatgaa ccgcaaacgt aaccgttggt ggctgcaagc tctgcacaaa    180
caagttgaaa taaaacagtt caaatngagg aaccaattat gggtattaca tataacataa    240
tcatggttca tgcacatacc gttattctgc aatgaatatt aagatcatcg tgcatctgac    300
taagacggtt ctttgcaagt tcttcagctg cacatgc                             337
```

<210> SEQ ID NO 4
<211> LENGTH: 466
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (415)..(415)
<223> OTHER INFORMATION: n = a or g

<400> SEQUENCE: 4

```
caaacactat ttgactttga gggaatttgg attttttctta ctacgtgtag aattgtatta    60
agattctaaa ccaagtgatg ttgacatgaa ggtcttggtc ctaatcagtt ctcgtctaaa   120
tctactgnaa aaaatatgg cagattggat acaatgntaa tgcatgattc atgaatgtgc    180
tacaataaga caacacctgt caacacttgc aaaggtaca aggaagtggg aaagtgcaaa    240
tccatttcct tcggcatatc actttcaacc aattgacaat aatagagcaa acatcacaag    300
aaaatggcaa gtttcactag ttttttatta tgagacatat ttgaaatgat catggaagga    360
agggatggag attcagatgg gtgttctttg tcatcaggtt cttggatcta aaagngtggc    420
ttagtccatc tttgactttc aaaataagag aaacctctga ttagtt                  466
```

<210> SEQ ID NO 5
<211> LENGTH: 501
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (251)..(251)

```
<223> OTHER INFORMATION: n = a or g
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t

<400> SEQUENCE: 5
agaatatttg attatccagt gaagagctga gctcgtgaga tgtcacgtga ctagagagta      60
gcaaccacac gcgagtacta cgcagctatg gatcagaatt acaactacta ataatcaaga    120
tttgcagatt tgtgaactca cacaccaa agactgaaac taaacaaaca aacaaacatc      180
gtcgtcttca tcgtcataat catctaattc ttcttctttg ttcagcttcc gtaaccgtaa    240
cgttaacgtc ntcgtcntcg tcatcgtcgt ttatcccaaa acgatggact tcaccacttt    300
cgcaaattcc atatcctatt ctcatgcaat tcctccaata caccttatc  gccttcaacc    360
ctctcctttt cccctcacc tcccattttc ggtacgtaat tctctctctc tctctctctc    420
tctctctctc tctatatata tatatatata tattattttt gttatttcat ttactgtgaa    480
ttttttgttg ttgtaattt n                                              501

<210> SEQ ID NO 6
<211> LENGTH: 501
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (251)..(251)
<223> OTHER INFORMATION: n = c or g

<400> SEQUENCE: 6
agcaaatgtc atcattgctt cagctttcat aatatgatca aactccctcg tatacaacag    60
ttgagtttga ttggttggac acaaagacat ggagttattc aagttatctt gacttttgtt   120
aagacattcc tctatggatg ttgaaggagg ggggttaaag ctctcaaagg aaggaaaccc   180
aacaggcaaa agtatttgac ctggaacatc tatcacacca cctggactgc tgttgacatc   240
tccacaatcc ngggcagaaa gcataagtgc ctgagattct gcagttcctg ggggcttgt    300
cagaaaatga ccacacaata agaaaccaat atacaagaga ccaagaagca gagagaaaaa   360
aacaatatta gaataataaa gaggaagagc ttataaattt gaagtattca tgagttaaac   420
aaaaagattc tgagtaaatt tatagaaatt atacaatcta tacagtcaac catatcttat   480
atccaaattt taatttgaag a                                             501

<210> SEQ ID NO 7
<211> LENGTH: 601
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (301)..(301)
<223> OTHER INFORMATION: n = a or c
<220> FEATURE:
<221> NAME/KEY: misc_feature
```

```
<222> LOCATION: (369)..(369)
<223> OTHER INFORMATION: n is a, c, g, or t

<400> SEQUENCE: 7
caatgcttca accgtgtttc tgacaagaag aaagaaagat gcaagacaca catgaacaac      60
gttaacccat gttgttttt gtttctctta tgtgtgtgga gccttgttgt gctcccctca     120
tgcgtgaggc cagttttgtg tgaagatgaa ggttgggatg gagtggttgt gacagcatca    180
aacctcttag cacttgaagc tttcaagcaa gagttggntg atccagaagg gttcttgcgg    240
agctggaatg acagtggcta tggagcttgt tccggaggtt gggttggaat caagtgtgct    300
nagggacagg ttattgtgat ccagcttcct tggaagggt tgaggggtcg aatcaccgac     360
aaaattggnc aacttcaagg cctcaggaag cttagtcttc atgataacca aattggtggt    420
tcaatccctt caactttggg acttcttccc aaccttagag gggttcagtt attcaacaat    480
aggcttacag gttccatacc tctttcttta ggtttctgcc ctttgcttca gtctcttgac    540
ctcagcaaca acttgctcac aggagcaatc ccttatagtc ttgctaattc cactaagctt    600
t                                                                    601

<210> SEQ ID NO 8
<211> LENGTH: 601
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (301)..(301)
<223> OTHER INFORMATION: n = g or a
<220> FEATURE:
<221> NAME/KEY: misc_feature
<222> LOCATION: (455)..(455)
<223> OTHER INFORMATION: n is a, c, g, or t

<400> SEQUENCE: 8
cttctggttt ttgattacat gtctaaagga agtcttgctt ctttcctaca tggtaagttt    60
cgtgtgctgt tctttcatta agtgttgtgn gtgctgttct ttaattataa tttggagttt   120
taccttagta atctgtataa ttctaatcgg agaacagtac aaacaaaaac acctaaggaa   180
cactatagca cctaaggaac aacaccttag ctttaatata ccatatcaat aagtgaatta   240
ttttcttgtt catcttgatg caggtggtgg aactgaaaca ttcattgatt ggccaacaag   300
natgaaaata gcacaagact tggcccgtgg cttgttctgc cttcattccc aggagaacat   360
catacatggg aacctcacat ccagcaatgt gttgcttgat gagaatacaa atgctaaaat   420
tgcagatttt ggtctttctc ggttgatgtc aactnctgct aattccaacg tgatagctac   480
agctggagca ttgggatacc gggcacctga gctctcaaag ctcaagaaag caaacactaa   540
aactgatatc tacagtcttg gtgttatctt gttagaactc taacgagga aatcacctgg    600
g                                                                    601

<210> SEQ ID NO 9
<211> LENGTH: 601
<212> TYPE: DNA
<213> ORGANISM: Artificial
<220> FEATURE:
<223> OTHER INFORMATION: Molecular marker
<220> FEATURE:
```

<221> NAME/KEY: misc_feature
<222> LOCATION: (301)..(301)
<223> OTHER INFORMATION: n = a or c

<400> SEQUENCE: 9

```
tggtgcttgt tcaggaggtt gggttggaat caagtgtgct cagggacagg ttatcgtgat      60
ccagcttcct tggaagggtt tgaagggtcg aatcactgac aaaattggcc aacttcaagg     120
ccttaggaag cttagtcttc atgataacca aattggtggt tcaatccctt caactttggg     180
acttcttccc aaccttagag gggttcagtt attcaacaat aggttaactg gttccatccc     240
ttcttcttta ggtttctgtc ctttgcttca gtctcttgac ctcagcaaca acttgctcac     300
nggagcaatc ccttatagcc ttgccaattc caccaagctt tattggctta acttgagttt     360
caactccttc tctggtactt taccaactag cctaactcac tcattttctc tcactttcct     420
ttctcttcaa aataataatc tttctggcaa ccttcctaac tcttggggtg ggagtcccaa     480
gagtggcttc tttaggctcc aaaatttgat cctagatcat aattttttca ctggtaatgt     540
tcctgcttct tgggtagct taagagagct cagtgagatt tcccttagtc ataataagtt     600
t                                                                    601
```

<210> SEQ ID NO 10
<211> LENGTH: 601
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (301)..(301)
<223> OTHER INFORMATION: n = a or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t

```
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t

<400> SEQUENCE: 10
ctggtccttc cccaccgacc tcacttcctc ctctaaccta atcgacctcg acctcgccac      60
cgtatccctc accggtccct tgccggacat tttcgacaaa ttcccttccc ttcaacacct     120
tcgcctctct tacaacaacc tcaccggcaa tttaccctcc tctttctccg ccgccaacaa     180
tctcgaaacg ctctggctca acaaccaggc cgccggcttg tccggtaccc tcctngtcct     240
ctccaacatg tcngcattaa accagtcctg gctcaataag aancagttca ccggttccat     300
nccggattth tcgcaatgca nggctttgtc tgacttgcag ctagggata accagttaac     360 tggtgtggtt cccgcttcnt tgacnagtct tccnagtttg aagaaagttt ctctggataa     420
naatgagctt caggggccng tgcccgtgtt tgggaaaggt gtgaatntta ctctcgatgg     480
gattaatagn ttttgtcttg anactcctgg gaattgtgat cccagggtga tggttttgct     540
gcngattgcc gaggcnttcg gntatccnat tcggttggcn gantcgtgga angggaatga     600
t                                                                     601

<210> SEQ ID NO 11
<211> LENGTH: 601
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (301)..(301)
```

<223> OTHER INFORMATION: n = a or c

<400> SEQUENCE: 11

```
aaaggataat tgagagtcag actctggtaa actgtctaaa aatggctcga catatctttt      60
gaggcatcaa ccaccaagaa ctatgcagca aaaccccccac ccaactcaac aaaacacgtg    120
aaaagagcaa aatataacat tgcaaagaaa tagccacaaa gaattttgaa gtagccatgt    180
atctaggaat tgagtatcaa ttattttccc ttcaactctt tctactttt ttttgtatgt     240
gagcgattac tctggtgaac tacttaaatt tgctgaacac cgaagcatga tattgaagta    300
ntaaccaaca gctataacca ccaaatacga gcatataaaa tatgaacttc aaaattaagg    360
cacaattgta caaaactaaa atcaaaggct ttctgtacct gcatactcag gtgcaagata    420
tccaaatgtt ccagccaacc gtgtctcaac agaatacttc ccatctggtg cattttaac    480
caacccaaaa tcagcaacct tgctctcat gtcatcgcct agtagtatgt ttgagggttt     540
taagtctcta tgaatgaagc tttgctgagc taaactgtgc aagtattcca cccccccgcgc   600
t                                                                  601
```

<210> SEQ ID NO 12
<211> LENGTH: 501
<212> TYPE: DNA
<213> ORGANISM: Artificial
<220> FEATURE:
<223> OTHER INFORMATION: Molecular marker
<220> FEATURE:
<221> NAME/KEY: misc_feature
<222> LOCATION: (251)..(251)
<223> OTHER INFORMATION: n = a or g
<220> FEATURE:
<221> NAME/KEY: misc_feature
<222> LOCATION: (317)..(318)
<223> OTHER INFORMATION: n is a, c, g, or t

<400> SEQUENCE: 12

```
aaggaacgcc gccgccggct tccgtccccg gcgcggtgtt caacgtggcc accagcatag     60
tcggcgccgg aatcatgtcg attccggcga tcatgaaggt tctcggcgta gttcccgctt    120
tcgcgatgat tctcgtggtg gccgtgctgg cggaactgtc cgtggacttc ctgatgcggt    180
tcacgcactc cggcgaaacg acgacgtacg ctggcgtcat gagggaggcg ttcggatcgg    240
gtggagcatt ngccgcgcaa gtttgcgtca tcatcaccaa cgttgggggt ttaattctct    300
accttatcat catcggnnac gtaacggaac ttttcccttt ttttttaatt tccttttctac   360
tgaattcgta aaaaggaaa aaaaaatgta gattttttca tgttttttggt ttggtatgct    420
tgttctgagt tttgccgggt tttcagtcag attcattttg attggtgaaa ttgttgctaa    480
taataagtga aatttgttt t                                              501
```

<210> SEQ ID NO 13
<211> LENGTH: 22
<212> TYPE: DNA
<213> ORGANISM: Artificial
<220> FEATURE:
<223> OTHER INFORMATION: Molecular marker

<400> SEQUENCE: 13

```
agcgaaagcc acttcatcaa tt                                             22
```

<210> SEQ ID NO 14
<211> LENGTH: 30
<212> TYPE: DNA
<213> ORGANISM: Artificial

```
<220> FEATURE:
<223> OTHER INFORMATION: Molecular marker

<400> SEQUENCE: 14
tgcgatatgc tctatacact gtaactattc                                    30

<210> SEQ ID NO 15
<211> LENGTH: 15
<212> TYPE: DNA
<213> ORGANISM: Artificial
<220> FEATURE:
<223> OTHER INFORMATION: Molecular marker

<400> SEQUENCE: 15
tgactcgtca cactt                                                    15

<210> SEQ ID NO 16
<211> LENGTH: 16
<212> TYPE: DNA
<213> ORGANISM: Artificial
<220> FEATURE:
<223> OTHER INFORMATION: Molecular marker

<400> SEQUENCE: 16
tgactcgtaa cacttt                                                   16

<210> SEQ ID NO 17
<211> LENGTH: 30
<212> TYPE: DNA
<213> ORGANISM: Artificial
<220> FEATURE:
<223> OTHER INFORMATION: Molecular marker

<400> SEQUENCE: 17
cactgaaata taaactcaag cactaattca                                    30

<210> SEQ ID NO 18
<211> LENGTH: 24
<212> TYPE: DNA
<213> ORGANISM: Artificial
<220> FEATURE:
<223> OTHER INFORMATION: Molecular marker

<400> SEQUENCE: 18
cctcatccaa catctacaaa acgt                                          24

<210> SEQ ID NO 19
<211> LENGTH: 20
<212> TYPE: DNA
<213> ORGANISM: Artificial
<220> FEATURE:
<223> OTHER INFORMATION: Molecular marker

<400> SEQUENCE: 19
tgaaaatgcg ttgtatgtac                                               20

<210> SEQ ID NO 20
<211> LENGTH: 22
<212> TYPE: DNA
<213> ORGANISM: Artificial
<220> FEATURE:
<223> OTHER INFORMATION: Molecular marker

<400> SEQUENCE: 20
attgaaaatg cattgtatgt ac                                            22
```

<210> SEQ ID NO 21
<211> LENGTH: 24
<212> TYPE: DNA
<213> ORGANISM: Artificial
<220> FEATURE:
<223> OTHER INFORMATION: Molecular marker

<400> SEQUENCE: 21
cggtatgtgc atgaaccatg atta                                          24

<210> SEQ ID NO 22
<211> LENGTH: 22
<212> TYPE: DNA
<213> ORGANISM: Artificial
<220> FEATURE:
<223> OTHER INFORMATION: Molecular marker

<400> SEQUENCE: 22
ctgcaagctc tgcacaaaca ag                                            22

<210> SEQ ID NO 23
<211> LENGTH: 16
<212> TYPE: DNA
<213> ORGANISM: Artificial
<220> FEATURE:
<223> OTHER INFORMATION: Molecular marker

<400> SEQUENCE: 23
aattggttcc tccatt                                                   16

<210> SEQ ID NO 24
<211> LENGTH: 17
<212> TYPE: DNA
<213> ORGANISM: Artificial
<220> FEATURE:
<223> OTHER INFORMATION: Molecular marker

<400> SEQUENCE: 24
taattggttc ctcgatt                                                  17

<210> SEQ ID NO 25
<211> LENGTH: 21
<212> TYPE: DNA
<213> ORGANISM: Artificial
<220> FEATURE:
<223> OTHER INFORMATION: Molecular marker

<400> SEQUENCE: 25
cagaggtttc tcttattttg a                                             21

<210> SEQ ID NO 26
<211> LENGTH: 18
<212> TYPE: DNA
<213> ORGANISM: Artificial
<220> FEATURE:
<223> OTHER INFORMATION: Molecular marker

<400> SEQUENCE: 26
gggatggaga ttcagatg                                                 18

<210> SEQ ID NO 27
<211> LENGTH: 16
<212> TYPE: DNA
<213> ORGANISM: Artificial
<220> FEATURE:
<223> OTHER INFORMATION: Molecular marker

```
<400> SEQUENCE: 27
actaagccac cctttt                                                        16

<210> SEQ ID NO 28
<211> LENGTH: 17
<212> TYPE: DNA
<213> ORGANISM: Artificial
<220> FEATURE:
<223> OTHER INFORMATION: Molecular marker

<400> SEQUENCE: 28
atggactaag ccactct                                                       17

<210> SEQ ID NO 29
<211> LENGTH: 20
<212> TYPE: DNA
<213> ORGANISM: Artificial
<220> FEATURE:
<223> OTHER INFORMATION: Molecular marker

<400> SEQUENCE: 29
gttcagcttc cgtaaccgta                                                    20

<210> SEQ ID NO 30
<211> LENGTH: 21
<212> TYPE: DNA
<213> ORGANISM: Artificial
<220> FEATURE:
<223> OTHER INFORMATION: Molecular marker

<400> SEQUENCE: 30
tgcgaaagtg gtgaagtcca t                                                  21

<210> SEQ ID NO 31
<211> LENGTH: 14
<212> TYPE: DNA
<213> ORGANISM: Artificial
<220> FEATURE:
<223> OTHER INFORMATION: Molecular marker

<400> SEQUENCE: 31
ttaacgtcat cgtc                                                          14

<210> SEQ ID NO 32
<211> LENGTH: 14
<212> TYPE: DNA
<213> ORGANISM: Artificial
<220> FEATURE:
<223> OTHER INFORMATION: Molecular marker

<400> SEQUENCE: 32
ttaacgtcgt cgtc                                                          14

<210> SEQ ID NO 33
<211> LENGTH: 22
<212> TYPE: DNA
<213> ORGANISM: Artificial
<220> FEATURE:
<223> OTHER INFORMATION: Molecular marker

<400> SEQUENCE: 33
gaactgcaga atctcaggca ct                                                 22

<210> SEQ ID NO 34
```

<210> SEQ ID NO 34
<211> LENGTH: 22
<212> TYPE: DNA
<213> ORGANISM: Artificial
<220> FEATURE:
<223> OTHER INFORMATION: Molecular marker

<400> SEQUENCE: 34
cctggactgc tgttgacatc tc                                              22

<210> SEQ ID NO 35
<211> LENGTH: 13
<212> TYPE: DNA
<213> ORGANISM: Artificial
<220> FEATURE:
<223> OTHER INFORMATION: Molecular marker

<400> SEQUENCE: 35
ctgccccgga ttg                                                        13

<210> SEQ ID NO 36
<211> LENGTH: 14
<212> TYPE: DNA
<213> ORGANISM: Artificial
<220> FEATURE:
<223> OTHER INFORMATION: Molecular marker

<400> SEQUENCE: 36
ttctgcccgg gatt                                                       14

<210> SEQ ID NO 37
<211> LENGTH: 19
<212> TYPE: DNA
<213> ORGANISM: Artificial
<220> FEATURE:
<223> OTHER INFORMATION: Molecular marker

<400> SEQUENCE: 37
ggagcttgtt ccggaggtt                                                  19

<210> SEQ ID NO 38
<211> LENGTH: 20
<212> TYPE: DNA
<213> ORGANISM: Artificial
<220> FEATURE:
<223> OTHER INFORMATION: Molecular marker

<400> SEQUENCE: 38
tccaaggaag ctggatcaca                                                 20

<210> SEQ ID NO 39
<211> LENGTH: 18
<212> TYPE: DNA
<213> ORGANISM: Artificial
<220> FEATURE:
<223> OTHER INFORMATION: Molecular marker

<400> SEQUENCE: 39
aatcaagtgt gctaaggg                                                   18

<210> SEQ ID NO 40
<211> LENGTH: 17
<212> TYPE: DNA
<213> ORGANISM: Artificial
<220> FEATURE:
<223> OTHER INFORMATION: Molecular marker

<400> SEQUENCE: 40
aatcaagtgt gctcagg                                                     17

<210> SEQ ID NO 41
<211> LENGTH: 18
<212> TYPE: DNA
<213> ORGANISM: Artificial
<220> FEATURE:
<223> OTHER INFORMATION: Molecular marker

<400> SEQUENCE: 41
aagccacggg ccaagtct                                                    18

<210> SEQ ID NO 42
<211> LENGTH: 21
<212> TYPE: DNA
<213> ORGANISM: Artificial
<220> FEATURE:
<223> OTHER INFORMATION: Molecular marker

<400> SEQUENCE: 42
tgcaggtggt ggaactgaaa c                                                21

<210> SEQ ID NO 43
<211> LENGTH: 19
<212> TYPE: DNA
<213> ORGANISM: Artificial
<220> FEATURE:
<223> OTHER INFORMATION: Molecular marker

<400> SEQUENCE: 43
tgtgctattt tcatccttg                                                   19

<210> SEQ ID NO 44
<211> LENGTH: 19
<212> TYPE: DNA
<213> ORGANISM: Artificial
<220> FEATURE:
<223> OTHER INFORMATION: Molecular marker

<400> SEQUENCE: 44
tgtgctattt tcattcttg                                                   19

<210> SEQ ID NO 45
<211> LENGTH: 24
<212> TYPE: DNA
<213> ORGANISM: Artificial
<220> FEATURE:
<223> OTHER INFORMATION: Molecular marker

<400> SEQUENCE: 45
cctttgcttc agtctcttga cctc                                             24

<210> SEQ ID NO 46
<211> LENGTH: 20
<212> TYPE: DNA
<213> ORGANISM: Artificial
<220> FEATURE:
<223> OTHER INFORMATION: Molecular marker

<400> SEQUENCE: 46
ttggtggaat tggcaaggct                                                  20

<210> SEQ ID NO 47
<211> LENGTH: 17
<212> TYPE: DNA

```
<213> ORGANISM: Artificial
<220> FEATURE:
<223> OTHER INFORMATION: Molecular marker

<400> SEQUENCE: 47
aacaacttgc tcacagg                                                    17

<210> SEQ ID NO 48
<211> LENGTH: 16
<212> TYPE: DNA
<213> ORGANISM: Artificial
<220> FEATURE:
<223> OTHER INFORMATION: Molecular marker

<400> SEQUENCE: 48
aacttgctca ccggag                                                     16

<210> SEQ ID NO 49
<211> LENGTH: 23
<212> TYPE: DNA
<213> ORGANISM: Artificial
<220> FEATURE:
<223> OTHER INFORMATION: Molecular marker

<400> SEQUENCE: 49
aaaccagtcc tggctcaata aga                                             23

<210> SEQ ID NO 50
<211> LENGTH: 20
<212> TYPE: DNA
<213> ORGANISM: Artificial
<220> FEATURE:
<223> OTHER INFORMATION: Molecular marker

<400> SEQUENCE: 50
agcgggaacc acaccagtta                                                 20

<210> SEQ ID NO 51
<211> LENGTH: 15
<212> TYPE: DNA
<213> ORGANISM: Artificial
<220> FEATURE:
<223> OTHER INFORMATION: Molecular marker

<400> SEQUENCE: 51
accggttcca taccg                                                      15

<210> SEQ ID NO 52
<211> LENGTH: 14
<212> TYPE: DNA
<213> ORGANISM: Artificial
<220> FEATURE:
<223> OTHER INFORMATION: Molecular marker

<400> SEQUENCE: 52
cggttccatt ccgg                                                       14

<210> SEQ ID NO 53
<211> LENGTH: 24
<212> TYPE: DNA
<213> ORGANISM: Artificial
<220> FEATURE:
<223> OTHER INFORMATION: Molecular marker

<400> SEQUENCE: 53
tgcaggtaca gaaagccttt gatt                                            24
```

```
<210> SEQ ID NO 54
<211> LENGTH: 24
<212> TYPE: DNA
<213> ORGANISM: Artificial
<220> FEATURE:
<223> OTHER INFORMATION: Molecular marker

<400> SEQUENCE: 54
gctgaacacc gaagcatgat attg                                              24

<210> SEQ ID NO 55
<211> LENGTH: 17
<212> TYPE: DNA
<213> ORGANISM: Artificial
<220> FEATURE:
<223> OTHER INFORMATION: Molecular marker

<400> SEQUENCE: 55
agctgttggt tagtact                                                      17

<210> SEQ ID NO 56
<211> LENGTH: 19
<212> TYPE: DNA
<213> ORGANISM: Artificial
<220> FEATURE:
<223> OTHER INFORMATION: Molecular marker

<400> SEQUENCE: 56
tatagctgtt ggttattac                                                    19

<210> SEQ ID NO 57
<211> LENGTH: 19
<212> TYPE: DNA
<213> ORGANISM: Artificial
<220> FEATURE:
<223> OTHER INFORMATION: Molecular marker

<400> SEQUENCE: 57
cgttggtgat gatgacgca                                                    19

<210> SEQ ID NO 58
<211> LENGTH: 21
<212> TYPE: DNA
<213> ORGANISM: Artificial
<220> FEATURE:
<223> OTHER INFORMATION: Molecular marker

<400> SEQUENCE: 58
ctgtccgtgg acttcctgat g                                                 21

<210> SEQ ID NO 59
<211> LENGTH: 13
<212> TYPE: DNA
<213> ORGANISM: Artificial
<220> FEATURE:
<223> OTHER INFORMATION: Molecular marker

<400> SEQUENCE: 59
cgcggccaat gct                                                          13
```

```
<210> SEQ ID NO 60
<211> LENGTH: 16
<212> TYPE: DNA
<213> ORGANISM: Artificial
<220> FEATURE:
<223> OTHER INFORMATION: Molecular marker

<400> SEQUENCE: 60
acttgcgcgg ctaatg                                                     16
```